United States Patent [19]
Pallos et al.

[11] Patent Number: 5,739,353
[45] Date of Patent: Apr. 14, 1998

[54] NOVEL N-ARYLINDOLES AND THEIR USE AS HERBICIDES

[75] Inventors: Ferenc M. Pallos, Walnut Creek; Christopher J. Mathews, San Francisco, both of Calif.

[73] Assignee: Zeneca Limited, London, England

[21] Appl. No.: 743,457

[22] Filed: Nov. 1, 1996

Related U.S. Application Data

[63] Continuation of Ser. No. 991,617, Dec. 31, 1992, Pat. No. 5,599,774, which is a continuation-in-part of Ser. No. 987,854, Dec. 9, 1992, Pat. No. 5,395,817, which is a continuation-in-part of Ser. No. 823,635, Jan. 22, 1992, abandoned.

[51] Int. Cl.$^6$ ............... C07D 209/04; C07D 209/12; C07D 209/14; C07D 209/18
[52] U.S. Cl. ............... 548/503; 548/469; 548/509; 548/510
[58] Field of Search ............... 548/469, 503, 548/509, 510

[56] References Cited

U.S. PATENT DOCUMENTS

| | | | |
|---|---|---|---|
| 4,156,734 | 5/1979 | Stone | 424/273 |
| 4,710,500 | 12/1987 | Perregaard | 514/254 |
| 5,216,001 | 6/1993 | Perregard et al. | 514/323 |

FOREIGN PATENT DOCUMENTS

| | | |
|---|---|---|
| 0 071 935 | 2/1983 | European Pat. Off. . |
| 0 186 367 | 7/1986 | European Pat. Off. . |
| 0 200 322 | 11/1986 | European Pat. Off. . |
| 0 351 641 | 1/1990 | European Pat. Off. . |
| 0 465 398 | 1/1992 | European Pat. Off. . |
| 0 501 269 | 9/1992 | European Pat. Off. . |
| 2 242 092 | 3/1975 | France . |
| 1 920 207 | 1/1970 | Germany . |
| 1 911 893 | 9/1970 | Germany . |
| 2 145 573 | 3/1973 | Germany . |
| 1 150 397 | 4/1969 | United Kingdom . |

OTHER PUBLICATIONS

*Chemical Abstracts* No. 159307v, Walsh, P.J. et al., "Generation, Native Ligand Trapping, and Nitrogen–Nitrogen Bond Cleavage Reactions of the First Monomeric eta. 1–hydrazido zirconocene Complex ($Cp_2Zr:NNPh_2$), A Zirconium Mediated Synthesis of Indoles", vol. 115, No. 15, 14 Oct. 1991, Columbus, OH, p. 958.

*Chemical Abstracts* No. 75226b, Barton D.H.R. et al., "Copper–Catalyzed Phenylation of Indoles by Triphenylbismuth bis (trifluoroacetate)", vol. 110, No. 9, 27 Feb. 1989, p. 624.

*Chemical Abstracts* No. 131506r, Nishio, T., "Photodesulfurization of Indoline–2–thiones: A Facile Synthesis of Indoles", vol. 108, No. 15, 11 Apr. 1988, Columbus, OH, p. 725.

*Chemical Abstracts* No. 197995k, Grinev, A.N. et al., "Synthesis and Biological Activity of 1–alkyl(aryl)5–methoxy(4,5–dimethoxy)–6–brimindole Derivatives", vol. 107, No. 21,23 Nov. 1987, Columbus, OH, p. 731.

*Chemical Abstracts* No. 24423r, Grinev, A.N. et al., "Synthesis and Study of the Antiviral Activity of Aminomethyl Derivatives of 4–hydroxy–5–methoxyindole", vol. 102, No. 3, 21 Jan. 1985, Columbus, OH, p. 674.

*Chemical Abstracts* No. 83313g, Andreani, A. et al., "Studies on Substances with Probable Antitumor Activity, II, Hydrazone derivatives of 2–chlorindoles", vol. 91, No. 11, 10 Sep. 1979, Columbus, OH, p. 67.

*Chemical Abstracts* No. 56749x, Khan, M.A. et al., "Arylindoles. II. N–Arylindole–3–Carboxaldehydes and their Derivatives", vol. 91, No. 7, 13 Aug. 1979, Columbus, OH, p. 683.

*Chemical Abstracts* No. 22728d, Grinev, A.N. et al., "Synthesis and Pharmacological Activity of Bis(diethyl)Amino Ethyl Esters of 2–Methyl–3–Carboxyindolyl–5–Hydroxyacetic Acids", vol. 90, No. 3, 15 Jan. 1979, Columbus, OH, p. 621.

*Chemical Abstracts* No. 127009m, Andreani, A. et al., "Nonsteroidal Antiflammatory Agents. 2. Synthesis and Biological Activity of 2–Chloroindolecarboxylic Acids", vol. 87, No. 17, 24 Oct. 1977, Columbus, OH, p. 27.

*Chemical Abstracts* No. 30797s, Griney, A.N. et al., "Synthesis of Aldehydes and Nitriles in the 5–Hydroxyindole Series", vol. 84, No. 5, 2 Feb. 1976, Columbus, OH, p. 436.

(List continued on next page.)

*Primary Examiner*—Deborah Lambkin
*Attorney, Agent, or Firm*—Marian T. Thomson

[57] ABSTRACT

This invention relates to substituted N-arylindoles, a process for producing them and their use as herbicides. In particular, this invention relates to substituted N-arylindoles of the formula

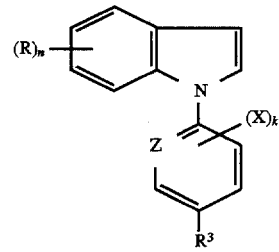

wherein R, $R^3$, X, Z, n and k are defined herein.

10 Claims, No Drawings

OTHER PUBLICATIONS

*Chemical Abstracts* No. 99772r, Elden, F. et al., "Synthesis of Antiphlogistically Active Indole Derivatives. I. Synthesis of 5–and 6–Hydroxyindole Derivatives by the Nenitzescu Procedure", vol. 74, No. 19, 10 May 1971, Columbus, OH, p. 487.

*Chemical Abstracts* No. 66732h, Grinev, A.N. et al., "Synthesis and Studies of Antiviral Properties in a Series of 2–Methyl–5–Hydroxyindole", vol. 72, No. 13, 30 Mar. 1970, Columbus, OH, p. 373.

*Chemical Abstracts* No. 86753g. Grinev, A.N. et al., "1–Aryl–5–Methoxyindole Derivatives", vol. 69, No. 21, 18 Nov. 1968, Columbus, OH, p. 8101.

*Chemical Abstracts* No. 173036j, Andreani, A. et al., "Indole Derivatives as Agrochemicals", vol. 110, No. 19, 8 May 1989, Columbus, OH, p. 756.

*Patent Abstracts of Japan*, vol. 13, No. 221 (c–598), 23 May 1989.

J. Perregaard et al., *J. Med. Chem* (1992) 35, 1092–1101, "Noncataleptogenic, Centrally Acting Dopamine D-2 and Serotonin 5-$HT_2$ Antagonists within a Series of 3–Substituted 1–(4–Fluorophenyl)–1 H–indoles".

M.A. Khan et al., J. Chem. Soc. (C), 1970, 85–91, "Synthesis of Heterocyclic Compounds. Part II. N–Arylazoles by Ullmann Condensation".

NOVEL N-ARYLINDOLES AND THEIR USE AS HERBICIDES

BACKGROUND AND SUMMARY OF THE INVENTION

This application is a continuation of application Ser. No. 07/991,617, filed Dec. 31, 1992, now U.S. Pat. No. 5,599,774, which is a continuation-in-part of application Ser. No. 07/987,854, filed Dec. 9, 1992, now U.S. Pat. No. 5,395,817, issued Mar. 7, 1995, which is a continuation-in-part of application Ser. No. 07/823,635, filed Jan. 22, 1992, now abandoned.

This invention relates to substituted N-arylindoles, a process for producing them and their use as herbicides. In particular, this invention relates to substituted N-arylindoles of the formula

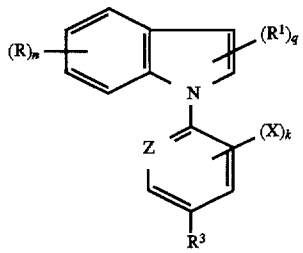

in which

R is hydrogen; halogen; nitro; cyano; alkyl; alkoxy; alkenyloxy; alkynyloxy; alkoxyalkyl; carbonylalkoxy; alkyloxyalkoxy; cyanoalkoxy; benzyloxy; alkoxycarbonylalkoxy; alkylcarbonylalkoxy; haloalkyl; hydroxalkyl; formyl; azido; carboxy and its salts; COOalkyl; amino; substituted amino wherein the substituents are alkyl, alkoxy, hydroxy, formyl, alkylcarbonyl, substituted alkylcarbonyl substituted with carboxy or alkoxycarboxy, alkylsulfonyl, haloalkylsulfonyl, aminocarbonyl, (di)alkylaminocarbonyl, alkoxycarbonyl, alkoxyalkyl, hydroxycarbonylalkyl, alkoxycarbonylalkyl, amino and (di)alkyl amino; carboxyamido; substituted carboxyamide wherein said substituents can be selected from alkyl, alkylsulfonyl, and haloalkylsulfonyl; sulfonamido wherein the N is substituted with hydrogen and/or alkyl; YR$^4$ wherein Y is O and S(O)$_m$ and R$^4$ is selected from the group hydrogen, alkyl, haloalkyl, cyanoalkyl, alkoxycarbonylalkyl, hydroxycarbonylalkyl and aminocarbonylalkyl wherein the N is substituted with hydrogen and/or alkyl;

n is 0 to 4 and
m is 0 to 2;

R$^1$ is hydrogen, alkyl, halogen, cyano, haloalkyl, alkoxy, and carboxy and its salts or esters;

q is 0 to 2;

X is hydrogen, halogen, cyano, nitro, alkylthio, alkylsulfinyl, alkylsulfonyl, and alkoxy;

k is 0 to 2;

Z is N and C—R$^2$; wherein R$^2$ is hydrogen, halogen, haloalkyl, cyano, nitro, alkythio, alkylsulfinyl, alkylsulfonyl and alkoxy;

R$^3$ is hydrogen, haloalkyl, haloalkoxy, cyano, halogen, and SO$_y$R$^5$ wherein R$^5$ is alkyl or haloalkyl and y is 0, 1 or 2; and agriculturally acceptable salts thereof.

DESCRIPTION OF THE INVENTION

Within the scope of the above formula, certain embodiments are preferred, as follows:

R is preferably halogen, nitro, alkoxy, cyano, lower alkyl, lower haloalkyl, amino, substituted amino, sulfonamido, alkylsulfonamido, alkythio, alkylsulfonyl, carboxyalkoxy and alkoxycarbonylalkoxy. Particularly preferred groups are fluoro, chloro, methoxy, alkoxyacetoxy, alkoxy-2-propionoxy, amino, sulfonamido, cyano and nitro, n is preferably 1 or 2.

R$^1$ is preferably hydrogen, methyl, halogen, and cyano. More preferably R$^1$ is hydrogen and halogen.

X is preferably hydrogen, chlorine and fluorine.

Z is preferably N, C—H or C-halogen.

R$^3$ is preferably trifluoromethyl.

The term "alkyl" and all groups containing alkyl portions are intended to include straight-chain, branched-chain and cyclic groups. Examples are methyl, ethyl, n-propyl, isopropyl, cyclopropyl, n-butyl and t-butyl. Each alkyl member may contain one to six carbon atoms. For example, (C$_1$-C$_6$)alkoxy(C$_1$-C$_6$)alkoxy; amino(C$_1$-C$_6$)alkylcarbonyl. The term "alkoxycarbonylalkoxy" includes alkyl groups that are straight-chain, branched-chain and cyclic with one to six carbon atoms. Examples are ethoxyacetoxy, ethoxy-2-propionoxy and methoxy-2-propionoxy.

In the above definitions, the term "halogen" includes fluoro, chloro, bromo and iodo groups. The term "haloalkyl" refers to the alkyl group substituted by one or more halogen atoms.

The compounds of the present invention have been found to be active herbicides, possessing utility as pre-emergence and post-emergence herbicides and useful against a wide range of plant species including broadleaf and grassy species. As mentioned hereinbelow, some of the compounds demonstrate selective control of plant species in certain crops, such as rice, corn and soybean.

This invention therefore also relates to a method for controlling undesirable vegetation comprising applying to a locus where control of such vegetation is desired, either prior or subsequent to the emergence of such vegetation, an herbicidally effective amount of a compound as described herein, together with an inert diluent or carrier suitable for use with herbicides.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and above-ground portions. The term "agriculturally acceptable salts" includes sodium, potassium, calcium, ammonium and magnesium salts.

The compounds of this invention are prepared by the following procedures:

GENERAL METHOD OF PREPARATION

The unarylated indoles as starting materials of the present invention are generally not novel and can generally be prepared by methods familiar to one skilled in the art or, in the alternative, they may be purchased. Indoles can be arylated on the nitrogen in the presence of bases, such as sodium hydride, potassium hydroxide and sodium hydroxide with an appropriate haloaryl or halo-heteroaryl group. One group of novel arylated indoles can be made by an analogus process as that described in Organic Synthesis Collective, Vol. VII, pg. 34, A. D. Batcho and W. Leimgruber, using appropriate 2-methylnitrobenzenes as starting materials.

The following examples teach the synthesis of a representative compound of this invention.

EXAMPLE 1

1-(3'-chloro-5'-trifluoromethyl-pyridyl-2')-4-chloroindole (Compound 34 in Table I)

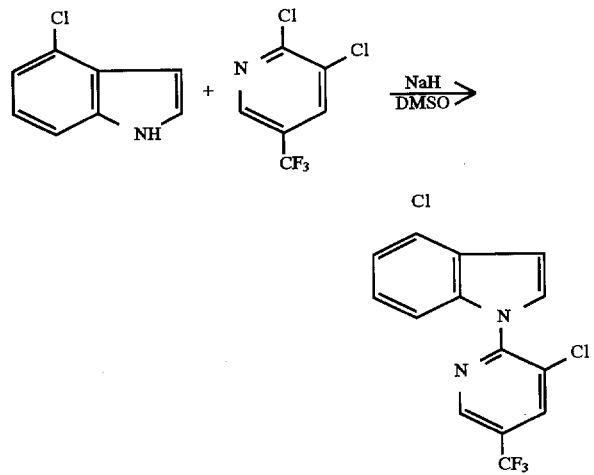

A mixture of 20.0 ml dimethylsulfoxide and 0.25 grams [g] (8.3 millimoles [mmol]) 80% sodium hydride suspension in oil was stirred at room temperature. To the mixture was added 1.0 g (6.6 mmol) 4-chloroindole and stirring continued at room temperature for 30 minutes. Slowly 1.4 g (6.6 mmol) 2,3-dichloro-5-trifluoromethyl pyridine was added, generating a slightly exothermic reaction. The mixture was stirred for 2 hours at room temperature.

Methanol (2.0 ml) was added and stirred for 5 minutes. Thereafter, water and methylene chloride were added. The organic phase was separated, washed with water, dried over anhydrous magnesium sulfate and stripped under vacuum to yield 1.4 g of an amber semi-solid. The proposed structure was determined by infrared spectroscopy, mass spectrometry and nuclear magnetic resonance spectroscopy.

EXAMPLE 2

1-[2',6'-dichloro-4'-trifluoromethylphenyl]-4-nitroindole (Compound 14 in Table 1)

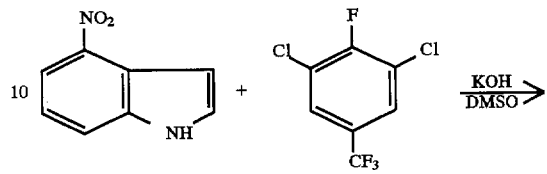

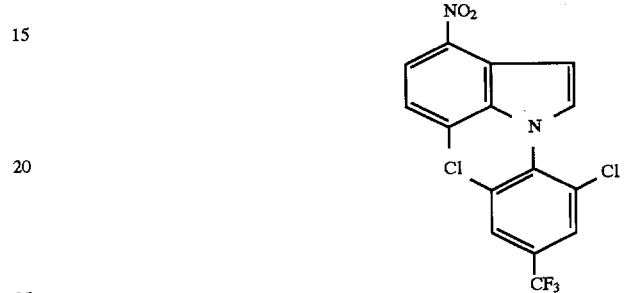

A mixture of 4-nitroindole (0.5 g, 3.0 mmol), potassium hydroxide pellets (0.7 g, 12.0 mmol) in 40.0 ml dimethylsulfoxide were stirred for 30 minutes at room temperature. Then 3,5-dichloro-4-fluorobenzotrifluoride was added and stirred at room temperature for 3 hours. Water and methylene chloride were added and the mixture was stirred for 10 minutes. The organic phase was separated, washed with water, dried and stripped under vacuum to yield 1.0 g of yellow solid of the desired product. The structure was confirmed by infra-red spectroscopy, mass spectrometry and nuclear magnetic resonance spectroscopy.

EXAMPLE 3

1-[2'-chloro-6'-fluoro-4'-trifluoromethylphenyl]-4-methoxyindole (Compound 18 in Table 1)

4-Methoxyindole (0.5 g, 3.4 mmol) and sodium hydride (80% dispersion in oil, 0.1 g, 3.9 mmol) were stirred together in dimethyl sulfoxide (10 ml) at room temperature for 30 minutes, and then 3-chloro-4,5-difluorobenzotrifluoride (0.73 g, 3.4 mmol) was added slowly. The mixture was stirred at room temperature for 2 hours, and then methanol (2 ml) was added. The mixture was partitioned between dichloromethane and water. The organic solution was dried over magnesium sulfate, filtered and the filtrate evaporated in vacuo, and the residue further purified by flash column chromatography on silica gel to give the title compound as a waxy solid (0.4 g). The structure was confirmed by infra-red spectroscopy, mass spectrometry and nuclear magnetic resonance spectroscopy.

EXAMPLE 4

1-[3'-chloro-5'-trifluoromethylpyridin-2-yl]-6-methoxyindole (Compound 32 in Table 1)

6-Methoxyindole was prepared according to the procedure of P. L. Feldman and H. Rapoport (Synthesis 735, 1986).

6-Methoxyindole (2.6 g, 18 mmol) and potassium hydroxide (4.0 g, 72 mmol) were stirred together in dimethyl sulfoxide (60 ml) at room temperature for 30 minutes, and then 2,3-dichloro-5-trifluoromethylpridine (4.0 g, 18 mmol) was added slowly. The mixture was stirred at room temperature for 4 hours, and then partitioned between diethyl ether and water. The ethereal solution was dried over magnesium sulfate, filtered and the filtrate evaporated in vacuo to give a dark solid residue (4.0 g). Further purification by flash column chromatography on silica gel gave the title compound (3.0 g) as a pale yellow solid, m.p. 68°–70° C.

EXAMPLE 5

1-[3'-chloro-5'-trifluoromethylpyridin-2-yl]-6-hydroxyindole (Compound 64 in Table 1)

1-[3'-chloro-5'-trifluoromethylpyridin-2-yl]-6-methoxyindole (1.9 g, 5.8 mmol) was dissolved in dichloromethane (50 ml) and the mixture cooled to −70° C. under an atmosphere of nitrogen. A solution of boron tribromide (1.0 ml, 11 mmol) in dichloromethane (10 ml) was added dropwise, and after stirring for 45 minutes at −70° C. a further quantity (0.5 ml, 5.5 mmol) of boron tribromide was added. The mixture was stirred for 15 minutes, and then the temperature was adjusted to 0° C. and methanol (10 ml) added. The mixture was stirred for 30 minutes, and allowed to warm to room temperature. The solvent was removed in vacuo, and the residue partitioned between diethyl ether and water. The ethereal solution was dried over magnesium sulfate, filtered and the filtrate evaporated under reduced pressure to give the title compound (1.3 g) as a waxy solid. The structure was confirmed by infra-red spectroscopy, mass spectrometry and nuclear magnetic resonance spectroscopy.

EXAMPLE 6

Methyl 2-[1-(3'-chloro-5'-trifluoromethylpyridin-2-yl)-indol-6-yloxy]propionate (Compound 46 in Table 1)

1-(3'-chloro-5-trifluoromethylpyridin-2-yl)-6-hydroxyindole (2.35 g, 7 mmol) and potassium carbonate (2.4 g, 17.5 mmol) were stirred together in N,N-dimethylformamide (40 ml) for 15 minutes, and then methyl 2-bromopropionate (1.2 g, 7 mmol) was added. The mixture was stirred at room temperature for 18 hours, and then partitioned between diethyl ether and water. The ethereal solution was dried over magnesium sulfate, filtered and the filtrate evaporated under reduced pressure to give the title compound (1.4 g) as a waxy solid. The structure was confirmed by infra-red spectroscopy, mass spectrometry and nuclear magnetic resonance spectroscopy.

EXAMPLE 7

2-[1-(3'-chloro-5'-trifluoromethylpyridin-2-yl)-indol-6-yloxy]propionic Acid (Compound 47 in Table 1)

Sodium hydroxide (4% aqueous solution, 25 ml) was added to a solution of methyl 2-[1-(3'-chloro-5'-trifluoromethylpyridin-2-yl)-indol-6-yloxy]propionate (0.6 g, 1.5 mmol) in isopropanol (25 ml) and the mixture stirred until thin layer chromatography showed no remaining starting material. The isopropanol was removed by evaporation in vacuo, and the remaining aqueous solution acidified with 2N aqueous hydrochloric acid and extracted with diethyl ether. The ethereal solution was dried over magnesium sulfate, filtered and the filtrate evaporated under reduced pressure to give the title compound (0.5 g) as a pale yellow solid, m.p. 155°–158° C. The structure was confirmed by infra-red spectroscopy, mass spectrometry and nuclear magnetic resonance spectroscopy.

EXAMPLE 8

1-[2',6'-dichloro-4'-trifluoromethylphenyl)-6-methoxyindole (Compound 15 in Table 1)

6-Methoxyindole (1.0 g, 6.8 mmol) and potassium hydroxide (1.5 g, 27 mmol) were stirred together in dimethyl sulfoxide (40 ml) at room temperature for 30 minutes, and then 3,5-dichloro-4-fluorobenzotrifluoride (1.6 g, 6.8 mmol) was added slowly. The mixture was stirred at room temperature for 17 hours, and then partitioned between diethyl ether and water. The ethereal solution was dried over magnesium sulfate, filtered and the filtrate evaporated in vacuo to give the title compound as a waxy solid (2.3 g). The structure was confirmed by infra-red spectroscopy, mass spectrometry and nuclear magnetic resonance spectroscopy.

EXAMPLE 9

Ethyl 2-[1-(2',6'-dichloro-4'-trifluoromethylphenyl)indol-6-yloxy]propionate (Compound 48 in Table 1)

1-(2',6'-dichloro-4'-trifluoromethylphenyl)-6-hydroxyindole (0.9 g, 2.6 mmol) and potassium carbonate (1.4 g, 10 mmol) were stirred together in N,N-dimethylformamide (50 ml) for 5 minutes, and then ethyl 2-bromopropionate (0.5 g, 2.6 mmol) was added. The mixture was stirred at room temperature for 18 hours, and then partitioned between diethyl ether and water. The ethereal solution was dried over magnesium sulfate, filtered and the filtrate evaporated under reduced pressure to give the title compound (1.2 g) as an amber colored oil. The structure was confirmed by infra-red spectroscopy, mass spectrometry and nuclear magnetic resonance spectroscopy.

EXAMPLE 10

2-[1-(2',6'-dichloro-4'-trifluoromethylphenyl)indol-6-yloxy]propionic Acid (Compound 49 in Table 1)

Sodium hydroxide (4% aqueous solution, 25 ml) was added to a solution of ethyl 2-[1-(2',6'-dichloro-4'-trifluoromethylphenyl)indol-6-yloxy]propionate (0.5 g, 1.5 mmol) in isopropanol (25 ml) and the mixture stirred for 10 minutes at room temperature. The isopropanol was removed by evaporation in vacuo, and the remaining aqueous solution acidified with 2N aqueous hydrochloric acid and extracted with diethyl ether. The ethereal solution was dried over magnesium sulfate, filtered and the filtrate evaporated under reduced pressure to give the title compound (0.4 g) as a pale yellow solid, m.p. 170°–174° C. The structure was confirmed by infra-red spectroscopy, mass spectometry and nuclear magnetic resonance spectroscopy.

EXAMPLE 11

1-(2',6'-dichloro-4'-trifluoromethylphenyl)-6-propargyloxyindole (Compound 56 in Table 1)

1-(2',6'-dichloro-4'-trifluoromethylphenyl)-6-hydroxyindole (1.3 g, 4 mmol) and potassium carbonate (1.4 g, 10 mmol) were stirred together in N,N'-dimethylformamide (50 ml) for 15 minutes, and then propargyl bromide (1.1 g, 8 mmol) was added. The mixture was stirred at room temperature for 4 hours, and then partitioned between diethyl ether and water. The ethereal solution was dried over magnesium sulfate, filtered and the filtrate evaporated under reduced pressure. The residue was further purified by flash column chromatography on silica gel to give the title compound (0.7 g) as a waxy solid. The structure was confirmed by infra-red spectroscopy, mass spectrometry and nuclear magnetic resonance spectroscopy.

EXAMPLE 12 ethyl 2-[1-(2',6'-dichloro-4'-trifluoromethylphenyl) indol-6-yloxy]acetate (Compound 54 in Table 1)

1-(2',6'-dichloro-4'-trifluoromethylphenyl)-6-hydroxyindole (3.5 g, 10 mmol) and potassium carbonate (3.6 g, 26 mmol) were stirred together in N,N-dimethylformamide (50 ml) for 30 minutes, and then ethyl bromoacetate (1.5 g, 10 mmol) was added. The mixture was stirred at room temperature for 18 hours, and then partitioned between diethyl ether and water. The ethereal solution was dried over magnesium sulfate, filtered and the filtrate evaporated under reduced pressure to give the title compound (3.0 g) as a waxy solid. The structure was confirmed by infra-red spectroscopy, mass spectrometry and nuclear magnetic resonance spectroscopy.

EXAMPLE 13

2-[1-(2',6'-dichloro-4'-trifluoromethylphenyl)indol-6-yloxy]acetic Acid (Compound 57 in Table 1)

Sodium hydroxide (4% aqueous solution, 50 ml) was added to a solution of ethyl 2-[1-(2',6'-dichloro-4'-trifluoromethylphenyl)indol-6-yloxy]acetate (3.0 g, 6.9 mmol) in isopropanol (50 ml) and the mixture stirred for 5 minutes at room temperature. The isopropanol was removed by evaporation in vacuo, and the remaining aqueous solution acidified with 2N aqueous hydrochloric acid and extracted with diethyl ether. The ethereal solution was dried over magnesium sulfate, filtered and the filtrate evaporated under reduced pressure. The residue was further purified by flash column chromatography on silica gel to give the title compound (1.0 g) as a colorless solid, m.p. 120°–123° C. The structure was confirmed by infra-red spectroscopy, mass spectrometry and nuclear magnetic resonance spectroscopy.

EXAMPLE 14

2-[1-(2',6'-dichloro-4'-trifluoromethylphenyl)indol-6-yloxy]acetamide (Compound 62 in Table 1)

Oxalyl chloride (0.8 ml, 9 mmol) was added to a mixture of 2-[1-(2',6'-dichloro-4'-trifluoromethylphenyl)indol-6-yloxy]acetic acid (1.7 g, 4 mmol) and N,N-dimethylformamide (1 drop) in dichloromethane (25 ml) and the mixture stirred at room temperature for 18 hours. The solvent was evaporated in vacuo and the residue taken up in diethyl ether. Ammonium hydroxide (aqueous solution, specific gravity 0.898, 20 ml) was added, and the mixture stirred vigorously for one hour. The mixture was poured into water and extracted with ethyl acetate. The organic extracts were combined, dried over magnesium sulfate, filtered and the filtrate evaporated under reduced pressure to give the title compound (1.3 g) as a pale yellow solid, m.p. 72°–75° C.

EXAMPLE 15

1-(3'-dichloro-5'-trifluoromethylpyridin-2-yl)-4-cyanoindole (Compound 61 in Table 1)

Step 1

N,N-Dimethylformamide dimethyl acetal (26.3 ml, 198 mmol) and pyrrolidine (6.9 ml, 83 mmol) were added to a solution of 2-cyano-6-nitrotoluene (10.8 g, 66 mmol) in N,N-dimethylformamide (200 ml), and the mixture heated to 105° C. for 3 hours under an atmosphere of nitrogen. The mixture was cooled to room temperature and partitioned between water and diethyl ether. The ethereal solution was dried over magnesium sulfate, filtered and the filtrate evaporated under reduced pressure to give a deep-red oil (10.6 g) used without further purification in the next step.

Step 2

The product from Step 1 was dissolved in ethyl acetate (150 ml) and 10% palladium on carbon (1.0 g) added. The mixture was stirred under an atmosphere of hydrogen at 40 p.s.i. for 2 hours. The catalyst was removed by filtration, then the filtrate evaporated and the residue further purified by flash column chromatography on silica gel to give 4-cyanoindole (4.0 g) as a yellow solid m.p. 115°–116° C.

Step 3

4-Cyanoindole (4.0 g, 28 mmol) and potassium hydroxide (6.3 g, 112 mmol) were stirred together in dimethyl sulfoxide (60 ml) at room temperature for 10 minutes, and then 2,3-dichloro-5-trifluoromethylpyridine (4.0 g, 18 mmol) was added slowly. The mixture was stirred at room temperature for 18 hours, and then partitioned between diethyl ether and water. The ethereal solution was dried over magnesium sulfate, filtered and the filtrate evaporated in vacuo to give a yellow solid residue (6.3 g). Further purification by flash column chromatography on silica gel gave 1-(3'-chloro-5'-trifluoromethylpyridin-2-yl)-4-cyanoindole (5.3 g) as a pale yellow solid, m.p. 109°–111° C.

EXAMPLE 16

4-amino-1-(3'-chloro-5'-trifluoromethylpyridin-2-yl)indole (Compound 78 in Table 1)

Step 1

N,N-Dimethylformamide dimethyl acetal (61 ml, 460 mmol) and pyrrolidine (15.9 ml, 190 mmol) were added to a solution of 2,6-dinitrotoluene (25.0 g, 140 mmol) in N,N-dimethylformamide (200 ml), and the mixture heated to 120° C. for 30 minutes under an atmosphere of nitrogen. The mixture was cooled to room temperature and partitioned between water and diethyl ether. The ethereal solution was dried over magnesium sulfate, filtered and the filtrate evaporated under reduced pressure to give a deep-red oil (18.5 g) used without further purification in the next step.

Step 2

The product from Step 1 was dissolved in ethyl acetate (200 ml) and 10% palladium on carbon (1.8 g) added. The mixture was stirred under an atmosphere of hydrogen at 40 p.s.i. for one hour. The catalyst was removed by filtration, then the filtrate evaporated and the residue further purified by flash column chromatography on silica gel to give 4-aminoindole (5.8 g) as a dark amorphous solid.

Step 3

4-Aminoindole (5.8 g, 44 mmol) and sodium hydride (80% dispersion in mineral oil, 1.3 g, 44 mmol) were stirred together in N,N-dimethylformamide (60 ml), with ice-bath cooling for 5 minutes, and then 2,3-dichloro-5-trifluoromethylpyridine (5,8 g, 44 mmol) was added slowly. The mixture was stirred at room temperature for 18 hours, and then a small quantity of methanol was added. The mixture was partitioned between diethyl ether and water. The ethereal solution was dried over magnesium sulfate, filtered and the filtrate evaporated in vacuo to give 4-amino-1-(3'-chloro-5'-trifluoromethylpyridin-2-yl)indole (6.5 g) as a dark solid.

EXAMPLE 17

4-acetamido-1-(3'-chloro-5'-trifluoromethylpyridin-2-yl)indole (Compound 80 in Table 1)

Acetic anhydride (1.3 g, 13 mmol) was added to a cooled (ice-bath) solution of 4-amino-1-(3'-chloro-5'-trifluoromethylpyridin-2-yl)indole (2.0 g, 6.4 mmol) in dichloromethane (50 ml), and the mixture stirred at room temperature overnight. The precipitate was collected by filtration, and washed with hexane to give the title compound (1.5 g) as a pink-colored solid, m.p. 208° C.

EXAMPLE 18

4-azido-1-(3'-chloro-5'-trifluoromethylpyridin-2-yl)indole (Compound 87 in Table 1)

4-Amino-1-(3'-chloro-5'-trifluoromethylpyridin-2-yl)indole (1.7 g, 5 mmol) was dissolved in 80% aqueous acetic acid (100 ml), and the mixture cooled to 0° C. in an ice-salt bath. A solution of sodium nitrite (0.4 g, 6 mmol) in water (1 ml) was added dropwise, and once the addition was complete the mixture was stirred for 5 minutes. A solution of sodium azide (0.4 g, 6 mmol) in water (1 ml) was added, and stirring continued for one hour. The acetic acid was removed in vacuo, and the residue partitioned between water and diethyl ether. The ethereal extract was washed with saturated aqueous sodium bicarbonate solution, dried over magnesium sulfate, filtered and the filtrate evaporated under reduced pressure to give the title compound (1.1 g) as a pale brown solid, m.p. 93°–95° C.

EXAMPLE 19

3-chloro-1-(3'-chloro-5'-trifluoromethylpyridin-2-yl)-4-methoxyindole (Compound 63 in Table 1)

Sulfuryl chloride (0.4 g, 3 mmol) was added to a cooled (ice-bath) solution of 1-(3'-chloro-5'-trifluoromethylpyridin-2-yl)-4-methoxyindole (1.0 g, 3 mmol) in diethyl ether (25 ml) and once the addition was complete, the cooling bath was removed, and the mixture stirred for 18 hours. A further quantity of sulfuryl chloride (0.04 g, 0.3 mmol) was added, and the mixture heated under reflux for 3 hours. The mixture was cooled, washed twice with water, dried over magnesium sulfate, filtered and the filtrate evaporated in vacuo. Further purification by flash column chromatography on silica gel gave the title compound (0.6 g) as a yellow waxy solid. The structure was confirmed by infra-red spectroscopy, mass spectrometry and nuclear magnetic resonance spectroscopy.

Compound 60, 1-(3'-chloro-5'-trifluoromethylpyridin-2-yl)2,3-dichloro-4-methoxyindole, m.p 140°–142° C. may be prepared in an analogous fashion, using excess sulfuryl chloride.

The following Table I depicts representative compounds of this invention:

TABLE I

COMPOUNDS

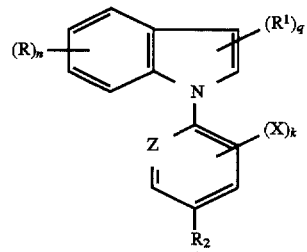

| Compound No. | R | Z | X | $R^1$ | $R^2$ | Properties Physical |
|---|---|---|---|---|---|---|
| 1 | H | C—Cl | 6-Cl | H | $CF_3$ | Semi-solid |
| 2 | 5-methoxy | C—Cl | 6-Cl | H | $CF_3$ | 70.0–73.0° C. |
| 3 | 6-$NO_2$ | C—Cl | 6-Cl | H | $CF_3$ | Semi-solid |
| 4 | 5-$NO_2$ | C—Cl | 6-Cl | H | $CF_3$ | Crystals |
| 5 | 5-F | C—Cl | 6-Cl | H | $CF_3$ | Semi-solid |
| 6 | 5-benzyloxy | C—Cl | 6-Cl | H | $CF_3$ | Semi-solid |
| 7 | 5,6-dimethoxy | C—Cl | 6-Cl | H | $CF_3$ | 118.0–120.0° C. |
| 8 | 4-F | C—Cl | 6-Cl | H | $CF_3$ | Oil |
| 9 | 6-F | C—Cl | 6-Cl | H | $CF_3$ | Oil |
| 10 | 5-$CH_3$ | C—Cl | 6-Cl | H | $CF_3$ | Semi-solid |
| 11 | 4-methoxy | C—Cl | 6-Cl | H | $CF_3$ | Semi-solid |
| 12 | 4-Cl | C—Cl | 6-Cl | H | $CF_3$ | Semi-solid |

TABLE I-continued

COMPOUNDS

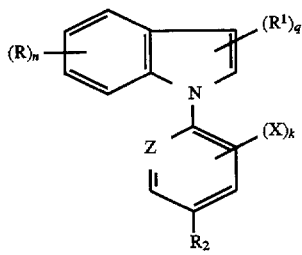

| Compound No. | R | Z | X | $R^1$ | $R^2$ | Properties Physical |
|---|---|---|---|---|---|---|
| 13 | 4-CH$_3$ | C—Cl | 6-Cl | H | CF$_3$ | Semi-solid |
| 14 | 4-NO$_2$ | C—Cl | 6-Cl | H | CF$_3$ | 125.0–130.0° C. |
| 15 | 6-methoxy | C—Cl | 6-Cl | H | CF$_3$ | Semi-solid |
| 16 | 6-CH$_3$ | C—Cl | 6-F | H | CF$_3$ | Semi-solid |
| 17 | 4-F | C—Cl | 6-F | H | CF$_3$ | Oil |
| 18 | 4-methoxy | C—Cl | 6-F | H | CF$_3$ | Semi-solid |
| 19 | 4-Cl | C—Cl | 6-F | H | CF$_3$ | Oil |
| 20 | 6-methoxy | C—Cl | 6-F | H | CF$_3$ | Semi-solid |
| 21 | H | N | 3-Cl | H | CF$_3$ | Semi-solid |
| 22 | 5-Br | N | 3-Cl | H | CF$_3$ | Semi-solid |
| 23 | 5-NO$_2$ | N | 3-Cl | H | CF$_3$ | Semi-solid |
| 24 | 5-methoxy | N | 3-Cl | H | CF$_3$ | 98.0–100.0° C. |
| 25 | 5-F | N | 3-Cl | H | CF$_3$ | Semi-solid |
| 26 | 5-benzyloxy | N | 3-Cl | H | CF$_3$ | Semi-solid |
| 27 | 4-F | N | 3-Cl | H | CF$_3$ | Oil |
| 28 | 6-F | N | 3-Cl | H | CF$_3$ | Oil |
| 29 | 5,6-dimethoxy | N | 3-Cl | H | CF$_3$ | 143.0–148.0° C. |
| 30 | 5-CH$_3$ | N | 3-Cl | H | CF$_3$ | Semi-solid |
| 31 | 4-CH$_3$ | N | 3-Cl | H | CF$_3$ | Semi-solid |
| 32 | 6-methoxy | N | 3-Cl | H | CF$_3$ | 65.0–70.0° C. |
| 33 | 6-CH$_3$ | N | 3-Cl | H | CF$_3$ | Semi-solid |
| 34 | 4-Cl | N | 3-Cl | H | CF$_3$ | Semi-solid |
| 35 | 4-CH$_3$COO | N | 3-Cl | H | CF$_3$ | Semi-solid |
| 36 | 4-methoxy | N | 3-Cl | H | CF$_3$ | Semi-solid |
| 37 | 5-benzyloxy | C—Cl | 6-Cl | H | CF$_3$ | 83.0–84.0° C. |
| 38 | 5-OCH$_3$ | C—Cl | 6-Cl | 2-CH$_3$ | CF$_3$ | Semi-solid |
| 39 | 5-OCH$_3$ | N | 3-Cl | 2-CH$_3$ | CF$_3$ | Semi-solid |
| 40 | 5-F | N | H | H | CF$_3$ | 65.0–70.0° C. |
| 41 | 4-CH$_3$ | N | H | H | CF$_3$ | 83.0–85.0° C. |
| 42 | 4-Cl | N | H | H | CF$_3$ | Semi-solid |
| 43 | 6-OCHC(=O)—OC$_2$H$_5$ \| CH$_3$ | N | 3-Cl | H | CF$_3$ | Oil |
| 44 | 6-OCH$_2$C(=O)—O—C$_2$H$_5$ | N | 3-Cl | H | CF$_3$ | Semi-solid |
| 45 | 6-OCH$_2$C(=O)—OH | N | 3-Cl | H | CF$_3$ | 110.0–115.0° C. |
| 46 | 6-OCHC(=O)—OCH$_3$ \| CH$_3$ | N | 3-Cl | H | CF$_3$ | Semi-solid |
| 47 | 6-OCH—COOH \| CH$_3$ | N | 3-Cl | H | CF$_3$ | 155.0–158.0° C. |
| 48 | 6-OCHC(=O)—OC$_2$H$_5$ \| CH$_3$ | C—Cl | 6-Cl | H | CF$_3$ | Oil |
| 49 | 6-OCH—C(=O)—OH \| CH$_3$ | C—Cl | 6-Cl | H | CF$_3$ | 170.0–174.0° C. |

TABLE I-continued

COMPOUNDS

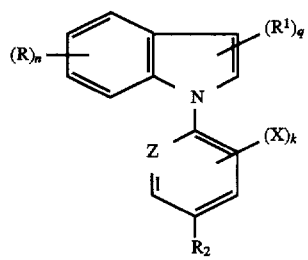

| Compound No. | R | Z | X | R$^1$ | R$^2$ | Properties Physical |
|---|---|---|---|---|---|---|
| 50 | 6-OCHC(CH$_3$)—OC$_2$H$_5$ (=O) | C—Cl | 6-F | H | CF$_3$ | Oil |
| 51 | 4-OCHC(CH$_3$)—OC$_2$H$_5$ (=O) | N | 3-Cl | H | CF$_3$ | Semi-solid |
| 52 | 6-NO$_2$ | N | 3-Cl | H | CF$_3$ | 132.0–133.0° C. |
| 53 | 6-NHSO$_2$CF$_3$ | N | 3-Cl | H | CF$_3$ | 218.0–222.0° C. |
| 54 | 6-OCH$_2$—C(=O)—OC$_2$H$_5$ | C—Cl | 6-Cl | H | CF$_3$ | Semi-solid |
| 55 | 6-OCHC(CH$_3$)—OCH$_3$ (=O) | C—Cl | H | H | CF$_3$ | Semi-solid |
| 56 | 6-OCH$_2$CCH | N | 3-Cl | H | CF$_3$ | Semi-solid |
| 57 | 6-OCH$_2$C(=O)—OH | C—Cl | 6-Cl | H | CF$_3$ | 120.0–123.0° C. |
| 58 | 6-NHC(=O)—C(=O)—OC$_2$H$_5$ | N | 3-Cl | H | CF$_3$ | 113.0–120.0° C. |
| 59 | 6-NHC(=O)—N—SO—C$_6$H$_5$ | N | 3-Cl | H | CF$_3$ | 160.0–170.0° C. |
| 60 | 4-OCH$_3$ | N | 3-Cl | 2,3-diCl | CF$_3$ | 140.0–142.0° C. |
| 61 | 4-CN | N | 3-Cl | H | CF$_3$ | 109.0–111.0° C. |
| 62 | 6-OCH$_2$—C(=O)—NH$_2$ | C—Cl | 6-Cl | H | CF$_3$ | 72.0–75.0° C. |
| 63 | 4-OCH$_3$ | N | 3-Cl | 3-Cl | CF$_3$ | Semi-solid |
| 64 | 6-OH | N | 3-Cl | H | CF$_3$ | Semi-solid |
| 65 | 6-OCHC(CH$_3$)—OC$_2$H$_5$ (=O) | C—Cl | H | H | CF$_3$ | Semi-solid |
| 66 | 5-CN | N | 3-Cl | H | CF$_3$ | 93.0–95.0° C. |
| 67 | 5-CN | C—Cl | 6-Cl | H | CF$_3$ | 145.0–147.0° C. |
| 68 | 4-NO$_2$ | N | 3-Cl | H | CF$_3$ | 135.0–137.0° C. |
| 69 | 5-Cl | N | 3-Cl | H | CF$_3$ | 50.0° C. |
| 70 | 5-Cl | C—Cl | 6-Cl | H | CF$_3$ | 95.0–96.0° C. |
| 71 | 6-NHC(=O)—CH$_2$—C(=O)—OC$_2$H$_5$ | N | 3-Cl | H | CF$_3$ | 133.0–135.0° C. |
| 72 | 4-NHSO$_2$CH$_3$ | N | 3-Cl | H | CF$_3$ | 180.0–182.0° C. |
| 73 | H | N | 3-Cl | 3-CN | CF$_3$ | 125.0–128.0° C. |
| 74 | 6-OSO$_2$CH$_3$ | N | 3-Cl | H | CF$_3$ | Semi-solid |

TABLE I-continued

COMPOUNDS

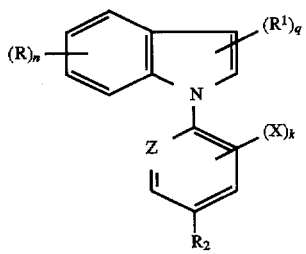

| Compound No. | R | Z | X | R¹ | R² | Properties Physical |
|---|---|---|---|---|---|---|
| 75 | 4-C(=O)—OCH₃ | N | 3-Cl | H | CF₃ | 105.0–107.0° C. |
| 76 | 4-C(=O)—OCH₃ | C—Cl | 6-Cl | H | CF₃ | Semi-solid |
| 77 | 4-C(=O)—OH | C—Cl | 6-Cl | H | CF₃ | 222.0–224.0° C. |
| 78 | 4-NH₂ | N | 3-Cl | H | CF₃ | Semi-solid |
| 79 | 4-NHC(=O)—CH₃ | N | 3-Cl | H | CF₃ | 208.0° C. |
| 80 | 4-N(CH₃)—C(=O)—CH₃ | N | 3-Cl | H | CF₃ | Semi-solid |
| 81 | 4-N(CH₃)—C(=O)—CF₃ | N | 3-Cl | H | CF₃ | Semi-solid |
| 82 | 4-Cl | C—Cl | 6-C | H | CF₃ | Oil |
| 83 | 4-OCH₃ | C—Cl | 6-C | H | CF₃ | Oil |
| 84 | 4-N(CH₃)₂ | N | 3-Cl | H | CF₃ | 80.0–82.0° C. |
| 85 | 4-NHCH₃ | N | 3-Cl | H | CF₃ | 85.0° C. |
| 86 | 4-CF₃ | N | 3-Cl | H | CF₃ | Oil |
| 87 | 4-N₃ | N | 3-Cl | H | CF₃ | 95–95° C. |
| 88 | 4-CN, 6-NH₂ | N | 3-Cl | H | CF₃ | 190° C. |

Herbicidal Screening Tests

The compounds listed in the foregoing table were tested for herbicidal activity by various methods and at various rates of application. The results of some of these tests are given below. As one skilled in the art is aware, the results obtained in herbicidal screening tests are affected by a number of factors that are not readily controllable. Environmental conditions, such as amount of sunlight and water, soil type, soil pH, temperature and humidity, are examples of such factors. Other factors which can affect test results are the depth of planting and the application rate of the herbicide, as well as the nature of the crops being tested. Results will also vary from crop to crop and within the crop varieties.

PRE-EMERGENCE HERBICIDAL SCREENING TEST

On the day preceding treatment, seeds of several different weed species were planted in sandy loam soil in individual rows using one species per row across the width of a flat. The grassy weeds planted were green foxtail (*Setaria viridis*), wild oat (*Avena fatua*), and watergrass (*Echinochloa crusgalli*). Broadleaf weeds utilized were wild mustard (*Brassica kaber*), velvetleaf (*Abutilon theophrasti*), and annual morningglory (*Ipomoea purpurea*). Additionally, seeded was yellow nutsedge (*Cyperus esculentus*). Ample seeds were planted to give about 20 to 40 seedlings per row, after emergence, depending upon the size of the plants.

Solutions of the test compounds were made by weighing out 400 mg of the test compound into a 60 ml wide-mouth bottle, then dissolving the compound in 25 ml acetone containing 1% TWEEN 20 (polyoxyethylene sorbitan monolaurate emulsifier). Additional solvents, not exceeding 5 ml, were used if needed to dissolve the compound. A 20.5 ml aliquot was then taken from the solution and diluted with 25 ml of an acetone:water mixture (19:1) containing 1% TWEEN 20 to form a sprayable solution.

The flats were placed in a greenhouse at 21°–29.5° C., and watered by sprinkling. One day after planting, the flats were sprayed with the spray solution calibrated to deliver 400 L/ha. The application rate was 4.0 kg/ha.

The flats were then returned to the greenhouse and water daily by sprinkling. The degree of weed control was estimated and recorded 3 weeks after treatment, as percentage control compared to the growth of the same species in an untreated check flat of the same age.

The percent control is the total injury to the plants due to all factors, including inhibited germination, killing of the plant tissue after emergence, stunting, malformation, chlorosis and other types of injury. The control ratings vary from 0 to 100 percent, where 0 represents no effect with growth equal to the untreated control, and 100 represents complete kill; a dash indicates that no test was performed at that level of application.

POST-EMERGENCE HERBICIDAL EVALUATION

The soil was prepared and seeded with the same varieties as described for the pre-emergence test. The flats were placed in the greenhouse at 21°–29° C. and watered by sprinkling. The seeds of the weed species were planted 10–12 days before treatment. The flats were sprayed with solution at a rate of 4 kg/ha, using a spray solution as prepared in the pre-emergence test.

The flats were returned to the greenhouse after spraying and watered daily without wetting the foliage. Three weeks after treatment the degree of weed control was estimated and recorded as percentage control compared to the growth of the same species in an untreated check flat of the same age. The percent control ratings were assigned on the basis as for the pre-emergence evaluation.

Table II lists the results of these tests, in terms of averages for the grasses and broadleaf weeds, with yellow nutsedge listed separately, in both pre- and post-emergence evaluations.

TABLE II

Pre-emergence Herbicidal Acitivity
Application Rate - 4.0 kg/ha
Abbreviations: AVG: Grass weeds averaged
AVB: Broadleaf weeds averaged
YNS: Yellow Nutsedge

| Compound | Pre-Emergence | | | Post-Emergence | | |
|---|---|---|---|---|---|---|
| No. | AVG | AVB | YNS | AVG | AVB | YNS |
| 1 | 30 | 71 | 0 | 8 | 61 | 0 |
| 2 | 41 | 58 | 0 | 40 | 70 | 0 |
| 3 | 3 | 3 | 0 | 20 | 51 | 0 |
| 4 | 63 | 10 | 0 | 51 | 63 | 5 |
| 5 | 86 | 30 | 0 | 33 | 73 | 10 |
| 6 | 0 | 0 | 0 | 5 | 8 | 0 |
| 7 | 75 | 86 | 0 | 23 | 95 | 10 |
| 8 | 96 | 91 | 0 | 41 | 70 | 10 |
| 9 | 3 | 6 | 0 | 5 | 61 | 0 |
| 10 | 70 | 66 | 5 | 13 | 70 | 5 |
| 11 | 95 | 95 | 0 | 60 | 99 | 5 |
| 12 | 98 | 100 | 0 | 76 | 100 | 5 |
| 13 | 86 | 86 | 0 | 20 | 78 | 5 |
| 14 | 5 | 0 | 0 | 1 | 51 | 0 |
| 15 | 100 | 100 | 0 | 86 | 100 | 10 |
| 16 | 73 | 100 | 5 | 33 | 100 | 10 |
| 17 | 93 | 99 | 5 | 70 | 71 | 10 |
| 18 | 98 | 100 | 5 | 81 | 100 | 30 |
| 21 | 71 | 36 | 0 | 26 | 43 | 0 |
| 22 | 15 | 0 | 0 | 13 | 36 | 0 |
| 23 | 95 | 61 | 0 | 26 | 63 | 0 |
| 24 | 6 | 0 | 0 | 3 | 0 | 0 |
| 25 | 100 | 56 | 0 | 86 | 68 | 10 |
| 26 | 0 | 0 | 0 | 0 | 3 | 0 |
| 27 | 100 | 66 | 5 | 81 | 86 | 20 |
| 28 | 40 | 3 | 0 | 20 | 48 | 0 |
| 29 | 61 | 48 | 5 | 23 | 61 | 5 |
| 30 | 68 | 5 | 0 | 38 | 55 | 5 |
| 31 | 96 | 73 | 0 | 56 | 71 | 10 |
| 32 | 100 | 86 | 5 | 92 | 68 | 25 |
| 33 | 70 | 48 | 0 | 26 | 66 | 10 |
| 34 | 100 | 100 | 30 | 100 | 100 | 25 |
| 35 | 0 | 3 | 0 | 10 | 6 | 0 |
| 36 | 100 | 96 | 10 | 93 | 98 | 30 |
| 37 | 0 | 3 | 0 | 0 | 13 | 0 |
| 38 | 0 | 0 | 0 | 3 | 0 | 0 |
| 39 | 6 | 10 | 0 | 8 | 40 | 0 |
| 40 | 5 | 0 | 0 | 3 | 8 | 0 |

TABLE II-continued

Pre-emergence Herbicidal Acitivity
Application Rate - 4.0 kg/ha
Abbreviations: AVG: Grass weeds averaged
AVB: Broadleaf weeds averaged
YNS: Yellow Nutsedge

| Compound | Pre-Emergence | | | Post-Emergence | | |
|---|---|---|---|---|---|---|
| No. | AVG | AVB | YNS | AVG | AVB | YNS |
| 41 | 16 | 1 | 0 | 5 | 1 | 0 |
| 42 | 85 | 48 | 5 | 38 | 81 | 5 |
| 60 | 1 | 1 | 0 | 5 | 38 | 0 |
| 61 | 93 | 100 | 5 | 65 | 83 | 5 |
| 63 | 25 | 5 | 0 | 6 | 63 | 5 |
| 64 | 0 | 0 | 0 | 3 | 26 | 5 |
| 68 | 30 | 15 | 0 | 6 | 3 | 0 |
| 72 | 0 | 0 | 0 | 5 | 6 | 0 |
| 73 | 0 | 0 | 0 | 1 | 6 | 0 |
| 78 | 0 | 0 | 0 | 16 | 26 | 0 |
| 79 | 0 | 0 | 0 | 0 | 8 | 0 |
| 80 | 0 | 0 | 0 | 5 | 11 | 0 |
| 81 | 6 | 3 | 0 | 3 | 43 | 0 |
| 82 | 98 | 100 | 0 | 68 | 96 | 10 |

In the following Table III, plants were treated essentially the same as plants in Table II, however, the flats were sprayed with a solution at a rate of 1 kg/ha. The results depicted in this Table do not average the herbicide results. The grasses and broad leaf weeds are listed separately for both pre-emergence and post-emergence. The weedy species are abbreviated as follows: green foxtail, SET; wild oat, AVF; watergrass, ECH; mustard, SIN; velvetleaf, ABT; annual morningglory, IPOSS and yellow nutsedge, YNS.

TABLE III

| Compound No. | Application | AVF | ECH | SET | ABT | IPOSS | SIN | YNS |
|---|---|---|---|---|---|---|---|---|
| 43 | PRE | 60 | 100 | 100 | 100 | 85 | 100 | 20 |
|  | POST | 30 | 100 | 100 | 100 | 100 | 100 | 85 |
| 44 | PRE | 0 | 0 | 50 | 100 | 100 | 70 | 5 |
|  | POST | 5 | 100 | 100 | 100 | 100 | 100 | 95 |
| 45 | PRE | 0 | 10 | 10 | 60 | 100 | 70 | 15 |
|  | POST | 10 | 100 | 100 | 100 | 100 | 100 | 80 |
| 46 | PRE | 60 | 100 | 100 | 100 | 60 | 100 | 10 |
|  | POST | 85 | 85 | 100 | 100 | 100 | 100 | 65 |
| 47 | PRE | 30 | 30 | 100 | 100 | 50 | 80 | 5 |
|  | POST | 90 | 90 | 100 | 100 | 100 | 100 | 100 |
| 48 | PRE | 5 | 15 | 100 | 100 | 80 | 100 | 0 |
|  | POST | 20 | 60 | 60 | 100 | 100 | 100 | 5 |
| 49 | PRE | 30 | 10 | 100 | 100 | 70 | 100 | 5 |
|  | POST | 10 | 95 | 60 | 100 | 100 | 100 | 30 |
| 50 | PRE | 5 | 5 | 75 | 100 | 30 | 100 | 0 |
|  | POST | 100 | 100 | 100 | 100 | 100 | 100 | 75 |
| 51 | PRE | 0 | 0 | 0 | 0 | 0 | 0 | 0 |
|  | POST | 0 | 0 | 10 | 60 | 10 | 0 | 0 |
| 52 | PRE | 5 | 5 | 50 | 20 | 0 | 5 | 0 |
|  | POST | 0 | 5 | 30 | 10 | 100 | 0 | 0 |
| 53 | PRE | 5 | 15 | 25 | 100 | 85 | 100 | 0 |
|  | POST | 10 | 40 | 75 | 100 | 100 | 100 | 10 |
| 54 | PRE | 0 | 0 | 5 | 100 | 70 | 100 | 0 |
|  | POST | 10 | 60 | 70 | 100 | 100 | 100 | 40 |
| 55 | PRE | 0 | 0 | 25 | 100 | 50 | 100 | 0 |
|  | POST | 5 | 15 | 60 | 100 | 100 | 100 | 20 |
| 56 | PRE | 0 | 0 | 60 | 100 | 100 | 100 | 0 |
|  | POST | 5 | 60 | 60 | 100 | 100 | 100 | 0 |
| 57 | PRE | 10 | 40 | 100 | 10 | 5 | 0 | 0 |
|  | POST | 15 | 30 | 60 | 100 | 100 | 15 | 5 |
| 58 | PRE | 0 | 0 | 75 | 0 | 50 | 100 | 5 |
|  | POST | 5 | 100 | 100 | 90 | 100 | 100 | 25 |
| 59 | PRE | 0 | 5 | 15 | 100 | 10 | 100 | 0 |
|  | POST | 5 | 5 | 60 | 95 | 30 | 60 | 5 |
| 62 | PRE | 0 | 0 | 50 | 100 | 100 | 100 | 0 |
|  | POST | 5 | 15 | 30 | 100 | 100 | 100 | 0 |

TABLE III-continued

| Compound No. | Application | AVF | ECH | SET | ABT | IPOSS | SIN | YNS |
|---|---|---|---|---|---|---|---|---|
| 65 | PRE | 5 | 10 | 75 | 100 | 90 | 100 | 0 |
|  | POST | 15 | 50 | 60 | 100 | 100 | 100 | 10 |
| 66 | PRE | 5 | 10 | 100 | 15 | 75 | 0 | 0 |
|  | POST | 10 | 30 | 70 | 100 | 100 | 15 | 5 |
| 67 | PRE | 0 | 0 | 15 | 60 | 50 | 75 | 0 |
|  | POST | 10 | 15 | 60 | 100 | 100 | 40 | 5 |
| 69 | PRE | 5 | 10 | 100 | 0 | 10 | 0 | 0 |
|  | POST | 0 | 20 | 10 | 70 | 75 | 0 | 0 |
| 70 | PRE | 0 | 5 | 50 | 15 | 40 | 5 | 0 |
|  | POST | 0 | 0 | 10 | 80 | 80 | 25 | 0 |
| 71 | PRE | 0 | 5 | 100 | 0 | 30 | 30 | 0 |
|  | POST | 0 | 25 | 85 | 100 | 100 | 100 | 10 |
| 74 | PRE | 25 | 90 | 100 | 90 | 100 | 5 | 5 |
|  | POST | 10 | 10 | 60 | 100 | 100 | 25 | 30 |
| 75 | PRE | 0 | 0 | 5 | 10 | 0 | 10 | 0 |
|  | POST | 5 | 5 | 10 | 60 | 95 | 5 | 0 |
| 76 | PRE | 0 | 0 | 5 | 0 | 0 | 0 | 0 |
|  | POST | 0 | 0 | 10 | 50 | 60 | 10 | 0 |
| 77 | PRE | 0 | 0 | 5 | 0 | 0 | 0 | 0 |
|  | POST | 0 | 0 | 0 | 0 | 5 | 0 | 0 |

The compounds of the present invention are useful as herbicides and can be applied in a variety of ways known to those skilled in the art, at various concentrations. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as amount 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, such as the Freons, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

The compounds of the present invention are also useful when combined with other herbicides and/or defoliants, dessicants, growth inhibitors, and the like. These other materials can comprise from about 5% to about 95% of the active ingredients in the formulations. These combinations frequently provide a higher level of effectiveness in controlling weeds and often provide results unattainable with separate formulations of the individual herbicides.

Examples of other herbicides, defoliants, dessicants and plant growth inhibitors with which the compounds of this invention can be combined are:

acetanilide herbicides such as alachlor, 2-chloro-2',6'-diethyl-N-(methoxymethyl) acetanilide; acetochlor, 2-chloro-N(ethoxymethyl)-6'-ethyl-o-acetotoluidide; metolachlor, 2-chloro-2'-methyl-6'-ethyl-N-methoxyisopropyl-2-acetanilide;

chlorophenoxy herbicides such as 2,4-D, 2,4,5-T, MCPA, MCPB, 2,4-DB, 2,4-DEB, 4-CPA, 2,4,5-TB, and silvex;

carbamate herbicides such as propham, chlorpropham, swep, and barban;

thiocarbamate and dithiocarbamate herbicides such as CDEC, metham-sodium, EPTC, diallate, PEBC, and vernolate;

substituted urea herbicides such as norea, dichloral, urea, chloroxuron, cycluron, fenuron, monuron, monuron TCA, diuron, linuron, monolinuron neburon, buturon and trimeturon;

symmetrical triazine herbicides such as simazine, chlorazine, desmetryne, norazine, ipazine, prometryn, atrazine, trietazine, simetone, prometone, propazine and ametryne;

chlorinated aliphatic acid herbicides such as TCA and dalapon;

chlorinated benzoic acid and phenylacetic acid herbicides such as 2,3,6-TBA, dicamba, tricamba, chloramben, fenac, PBA, 2-methoxy-3,6-dichlorophenyl acetic acid, 3-methoxy-2,6-dichlorophenyl acetic acid, 2-methoxy-3, 5,6-trichlorophenyl acetic acid, and 2,4-dichloro-3-nitro benzoic acid;

and such compounds as aminotriazole, maleic hydrazide, phenyl-mercury acetate, endothal, technical chlordane, CDCPA, diquat, erbon, DNC, DNBP, dichlobenil, DPA, diphenamide, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, sesone, terbacil, terbutol, TCBA, nitralin, sodium tetraborate, calcium cyanamide, S,S,S-tributylphosphorotrithioate and propanil, isopropyl amine salt of N-phosphonomethyl glycine, trimethylsulfonium salts of N-phosphonomethyl glycine.

These formulations can be applied to the areas where control is desired by conventional methods. Dust and liquid compositions, for example, can be applied by the use of power-dusters, boom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following are examples of typical formulations:

| 5% dust: | 5 parts active compound |
| | 95 parts talc |
| 2% dust | 2 parts active compound |
| | 1 part highly dispersed silicic acid |
| | 97 parts talc |

These dusts are formed by mixing the components then grinding the mixture to the desired particle size.

| 5% granules: | 5 parts active compound |
| | 0.25 part epichlorohydrin |
| | 0.25 part cetyl polyglycol ether |
| | 3.5 parts polyethylene glycol |
| | 91 part kaolin (particle size 0.3–0.8 mm) |

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

| Wettable powders: | |
| --- | --- |
| 70%: | 70 parts active compound |
| | 5 parts sodium dibutylnaphthylsulfonate |
| | 3 parts naphthalenesulfonic acid/phenolsulfonic acid/formaldehyde condensate (3:2:1) |
| | 10 parts kaolin |
| | 12 parts champagne chalk |
| 40%: | 40 parts active compound |
| | 5 parts sodium lignin sulfonate |
| | 1 part sodium dibutylnaphthalene sulfonic acid |
| | 54 parts silicic acid |
| 25%: | 25 parts active compound |
| | 4.5 parts calcium lignin sulfate |
| | 1.9 parts champagne chalk/hydroxyethyl cellulose (1:1) |
| | 1.5 parts sodium dibutylnaphthalene sulfonate |
| | 19.5 silicic acid |
| | 19.5 parts champagne chalk |
| | 28.1 parts kaolin |
| 25%: | 25 parts active compound |
| | 2.5 parts isooctylphenoxy-polyethylene-ethanol |
| | 1.7 parts champagne chalk/hydroxyethyl cellulose (1:1) |
| | 8.3 parts sodium aluminum silicate |
| | 16.5 parts kieselguhr |
| | 46 parts kaolin |
| 10%: | 10 parts active compound |
| | 3 parts of a mixture of sodium salts of saturated fatty alcohol sulfates |
| | 5 parts naphthalenesulfonic acid/formaldehyde condensate |
| | 82 parts kaolin |

These wettable powders are prepared by intimately mixing the active compounds with the additives in suitable mixers, and grinding the resulting mixture in mills or rollers.

| Emulsifiable concentrate: | |
| --- | --- |
| 25%: | 25 parts active substance |
| | 2.5 parts epoxidized vegetable oil |
| | 10 parts of an alkylarylsulfonate/fatty alcohol polyglycol ether mixture |
| | 5 parts dimethylformamide |
| | 57.5 parts xylene |

What is claimed is:
1. A compound having the formula

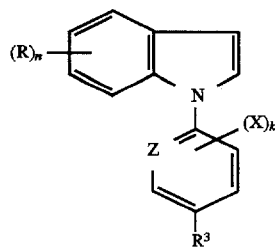

in which:

R is halogen; nitro; cyano; (C$_1$–C$_6$)alkyl; (C$_1$–C$_6$)alkoxy; (C$_2$–C$_6$)alkenyloxy; (C$_2$–C$_6$)-alkynyloxy; (C$_1$–C$_6$) alkoxy(C$_1$–C$_6$)alkyl; carbonyl(C$_1$–C$_6$)alkoxy; (C$_1$–C$_6$) alkyloxy(C$_1$–C$_6$)alkoxy; cyano(C$_1$–C$_6$)alkoxy; benzyloxy; (C$_1$–C$_6$)alkoxycarbonyl(C$_1$–C$_6$)alkoxy; (C$_1$–C$_6$)

alkylcarbonyl($C_1$–$C_6$)alkoxy; halo($C_1$–$C_6$)alkyl; hydroxy($C_1$–$C_6$)alkyl; formyl; azido; carboxy or a salt thereof; amino; substituted amino having at least one substituent selected from the group consisting of ($C_1$–$C_6$)alkyl, ($C_1$–$C_6$)alkoxy, hydroxy, formyl, ($C_1$–$C_6$)alkylcarbonyl, substituted ($C_1$–$C_6$) alkylcarbonyl substituted with carboxy or ($C_1$–$C_6$) alkoxycarboxy, ($C_1$–$C_6$)alkylsulfonyl, halo($C_1$–$C_6$) alkylsulfonyl, aminocarbonyl, (di) ($C_1$–$C_6$) alkylaminocarbonyl, ($C_1$–$C_6$)alkoxycarbonyl, ($C_1$–$C_6$) alkoxy($C_1$–$C_6$)alkyl, hydroxycarbonyl($C_1$–$C_6$)alkyl, ($C_1$–$C_6$)alkoxycarbonyl($C_1$–$C_6$)alkyl, amino and (di) ($C_1$–$C_6$)alkylamino; carboxyamido; substituted carboxyamido having at least one substituent selected from the group consisting of ($C_1$–$C_6$)alkyl, ($C_1$–$C_6$) alkylsulfonyl, and halo($C_1$–$C_6$)alkylsulfonyl; sulfonamido wherein the N is unsubstituted or substituted with ($C_1$–$C_6$)alkyl; $YR^4$ wherein Y is O or $S(O)_m$ and $R^4$ is selected from the group consisting of hydrogen, ($C_1$–$C_6$)alkyl, halo($C_1$–$C_6$)alkyl, cyano($C_1$–$C_6$)alkyl ($C_1$–$C_6$)alkoxycarbonyl($C_1$–$C_6$)alkyl, hydroxycarbonyl($C_1$–$C_6$)alkyl and aminocarbonyl ($C_1$–$C_6$)alkyl wherein the N is unsubstituted or substituted with ($C_1$–$C_6$)alkyl;

n is 0 to 4 and m is 0 to 2;

X is halogen, cyano, nitro, ($C_1$–$C_6$)alkylthio, ($C_1$–$C_6$) alkylsulfinyl, ($C_1$–$C_6$)alkyl sulfonyl, or ($C_1$–$C_6$) alkoxy;

k is 0 to 2;

Z is C—$R^2$; wherein $R^2$ is hydrogen, halogen, halo ($C_1$–$C_6$)alkyl, cyano, nitro, ($C_1$–$C_6$)alkylthio, ($C_1$–$C_6$) alkylsulfinyl, ($C_1$–$C_6$)alkylsulfonyl, or ($C_1$–$C_6$)alkoxy;

$R^3$ is halo($C_1$–$C_6$)alkyl, halo($C_1$–$C_6$)alkoxy, cyano, halogen, or $SO_yR^5$ wherein $R^5$ is ($C_1$–$C_6$)alkyl or halo($C_1$–$C_6$)alkyl and y is 0, 1 or 2;

with the proviso that when n and k are both zero and $R^2$ is hydrogen, $R^3$ is not cyano;

with the further proviso that when n is 0 or 1, k is 0 and $R^2$ is hydrogen, $R^3$ is not fluoro or $CH_2Cl$, or an agriculturally acceptable salt thereof.

2. A compound according to claim 1 having the formula

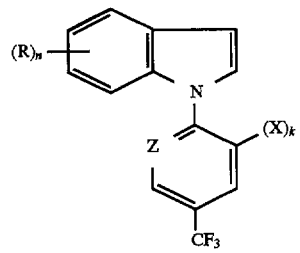

in which:

R is halogen, ($C_1$–$C_6$)alkyl, ($C_1$–$C_6$)alkoxy, ($C_2$–$C_6$) alkenyloxy, ($C_2$–$C_6$)alkynyloxy, acetoxy, amino, substituted amino, sulfonamido, ($C_1$–$C_6$) alkylsulfonamido, carboxy($C_1$–$C_6$)alkoxy, ($C_1$–$C_6$) alkoxycarbonylamide, ($C_1$–$C_6$)alkoxycarbonyl($C_1$–$C_6$) alkoxy, ($C_1$–$C_6$)alkoxy($C_1$–$C_6$)alkoxy, cyano cyano ($C_1$–$C_6$)alkoxy, halogen, halo($C_1$–$C_6$)alkyl, nitro ($C_1$–$C_6$)alkylthio and ($C_1$–$C_6$)alkylsulfonate;

n is 0 to 2;

k is 0 or 1, and when k is 1, X is halogen or halo($C_1$–$C_6$) alkyl; and

Z is C—$R^2$, wherein $R^2$ is hydrogen, halogen or halo ($C_1$–$C_6$)alkyl.

3. A compound according to claim 2 wherein n is 1 or 2, k is 0 or 1 and when k is 1, X is chlorine or fluorine, and Z is C-halogen, C-hydrogen, or C-trifluoromethyl.

4. A compound according to claim 3 wherein R is halogen, $C_1$–$C_3$ alkyl, $C_1$–$C_3$ alkoxy, amino, substituted amino, cyano, nitro or alkoxycarbonylalkoxy.

5. A compound according to claim 4 wherein R is halogen.

6. A compound according to claim 3 wherein R is substituted at the 4-, 5- or 6-position and n is 1.

7. A compound according to claim 4 wherein R is $C_1$–$C_3$ alkyl.

8. A compound according to claim 4 wherein R is $C_1$–$C_3$ alkoxy.

9. A compound according to claim 4 wherein R is alkoxycarbonylalkoxy.

10. A compound according to claim 5 wherein R is fluoro or chloro.

* * * * *